United States Patent [19]
Gorog

[11] Patent Number: 5,599,718
[45] Date of Patent: Feb. 4, 1997

[54] MEASUREMENT OF THE THROMBOLYTIC ACTIVITY OF BLOOD

[76] Inventor: Diana Gorog, 20 Grenville Court, London SE19 1LS, United Kingdom

[21] Appl. No.: 107,672

[22] PCT Filed: Dec. 16, 1992

[86] PCT No.: PCT/GB92/02328

§ 371 Date: Aug. 18, 1993

§ 102(e) Date: Aug. 18, 1993

[87] PCT Pub. No.: WO93/12423

PCT Pub. Date: Jun. 24, 1993

[30] Foreign Application Priority Data

Dec. 19, 1991 [GB] United Kingdom .................. 9126987

[51] Int. Cl.⁶ .................................................. G01N 33/86
[52] U.S. Cl. ............................. 436/69; 436/63; 436/164; 422/73; 422/99; 422/102
[58] Field of Search ................................ 422/73, 81, 99, 422/100, 102; 436/63, 69, 148, 164; 435/13; 73/64.11, 54; 604/31, 251, 253

[56] References Cited

U.S. PATENT DOCUMENTS

| | | | |
|---|---|---|---|
| 3,911,728 | 10/1975 | Fixot | 73/55 |
| 4,604,894 | 8/1986 | Kratzer et al. | 73/64.41 |
| 4,780,418 | 10/1988 | Kratzer | 73/64.41 |
| 4,867,069 | 10/1989 | Jochimsen | 422/73 |
| 4,952,373 | 8/1990 | Sugarman et al. | 422/99 |
| 5,047,211 | 9/1991 | Sloane et al. | 73/64.41 |
| 5,051,239 | 9/1991 | von der Goltz | 422/73 |
| 5,207,988 | 5/1993 | Lucas | 422/73 |
| 5,293,772 | 3/1994 | Carr, Jr. | 73/64.41 |
| 5,296,379 | 3/1994 | Gorog et al. | 73/64.41 |

FOREIGN PATENT DOCUMENTS

| | | |
|---|---|---|
| 0111942 | 12/1983 | European Pat. Off. . |
| 0129425 | 6/1984 | European Pat. Off. . |
| 0316599 | 10/1988 | European Pat. Off. . |

*Primary Examiner*—Steven Weinstein
*Assistant Examiner*—Lien Tran
*Attorney, Agent, or Firm*— Myers, Liniak & Berenato

[57] ABSTRACT

An in vitro method of monitoring thrombolysis of an occlusive thrombus formed under conditions which simulate in vivo is described. Thrombus is formed in a capillary tube by causing blood to flow under pressure from a non-anticoagulated supply thereof through the capillary lumen and into a reservoir in such a way that the thrombus forms solely by shear-stress. Formation of the thrombus is detected and the pressure on the tube is reduced, the reduced pressure being maintained for a predetermined period of time during which the thrombus stabilises. The pressure is then applied on the thrombus across anticoagulated blood from the same sample and lysis of the thrombus is detected. Preferably the supply of anticoagulated blood is produced by mixing the blood exiting the capillary tube with anticoagulant in the reservoir, the blood flow direction being reversed once thrombus stabilisation has taken place. The reservoir may be connected to a second reservoir by a connecting line. A photosensor monitoring blood in the line is then capable of detecting both formation of the thrombus and lysis of the thrombus.

27 Claims, 1 Drawing Sheet

MEASUREMENT OF THE THROMBOLYTIC ACTIVITY OF BLOOD

BACKGROUND OF THE INVENTION

This invention relates to an in vitro method of measuring the thrombolytic activity of whole blood, in particular it relates to a method for measuring the lysis of an occlusive platelet-rich thrombus formed in vitro under conditions which simulate those in vivo and an apparatus for implementation of the method.

The ability to measure the thrombolytic activity of blood is extremely important, for example, it is now considered that whether or not spontaneous thrombolysis can occur in a patient is a main determinant of whether or not a patient will survive an acute myocardial infarction. (Swan, H. J. C. Acute Myocardial Infarction: A failure to timely, spontaneous thrombolysis. Journal of the American College of Cardiology 13:1435–37 (1989).) Furthermore, excessive thrombolysis which can occur during cardiopulmonary bypass is regarded as the main cause of severe bleeding after a successful operation.

Furthermore, thrombolytic therapy, i.e. the treatment of patients with thrombolytic agents, for example, tissue type plasminogen activator (t-PA) or streptokinase which simulate the natural thrombolysis, is at present the most efficient method of treating life-threatening arterial thrombotic disorders. The efficiency (patency-rate) and side effects, i.e. bleeding, of thrombolytic therapy are dose-related. Moreover, the amount of thrombolytic agent needed for a particular patient is found to vary widely, depending on a number of factors. A technique is therefore required to allow rapid and ready monitoring of the effect on a patient of the therapy.

There are many known techniques for measuring fibrinolysis. Overall fibrinolysis assays such as the lysis time of plasma proteins, e.g. euglobulin and fibrinogen, whole plasma or whole blood are laborious and time-consuming and therefore rarely used in clinical practice. Fibrinolytic status is normally assessed by the factorial approach, whenever at least half a dozen plasma variables are measured. While the list of the necessary variables is constantly increasing, the assessment of the overall status from the individual variables is extremely difficult.

In contrast to fibrinolysis, there is no technique of thrombolysis measurement in use in clinical practice. Thrombolysis, i.e. disintegration of an arterial thrombus, consisting of a mass of tightly packed blood cells of which the main are platelets but some are white cells is essentially different from fibrinolysis. Due to inhibitors released from the platelet mass, such a thrombus can be much more resistant to lysis than a plasma clot.

In order to measure thrombolysis in-vitro, a thrombus must first be formed. For the measurement to be meaningful, i.e. to give an accurate indication of the real in vivo situation, the thrombus must be formed in a physiologically relevant manner.

The conditions therefore should be an accurate reproduction of those found in vivo. In particular, it is now considered that one of the most relevant factors which initiates a thrombotic event are the haemodynamic forces, i.e. shear-stress. During formation of the thrombus, thrombin is generated which, together with shear-forces, plays the decisive role in the process. Thrombin amplifies platelet aggregation and by forming fibrin, confers structural stability to the thrombus.

Accordingly, for formation to be achieved in a physiologically relevant manner, the blood sample in which the thrombus is formed should be non-anticoagulated, as thrombin does not form in anticoagulated blood. Also, thrombus formation should be initiated entirely by shear-forces, as employing other thrombogenic stimuli makes the test irrelevant to physiology.

The Applicant is aware of only two known methods for measuring thrombolysis, described respectively in European Patent Application 0129425 and International Patent Application PCT/GB87/00633. In the methods described in both these applications, thrombi are formed in small holes punched in polyethylene tubing through which blood is perfused. Thrombolysis of the blood can be measured by causing the blood flow in the tube to cease and observing the dislodgement of the thrombi and consequent "rebleeding".

Although these known methods satisfy the above criteria, they suffer from a number of inherent shortcomings. The most serious one is that in the tubing through which the blood is perfused and the thrombus is formed, blood clots both behind and in front of the thrombus. Thus, when back-pressure is applied to dislodge the thrombus (thrombolysis), transmission of the pressure is blocked or greatly impeded by the resistance of the clotted blood. The back pressure on the thrombi is accordingly uneven and variable.

Moreover, the interaction between the polyethylene and the thrombus mass is weak. Accordingly, changes in the perfusion pressure once coagulation has begun as a result of intermittent movement of the partially clotted blood in the tubing, can cause expulsion of the fragile thrombi without real lysis.

The result is that thrombolysis cannot be monitored in a relevant and reproducible way.

A further shortcoming with the known methods for measuring thrombolysis resides in the fact that a thrombus is much more resistant to lysis in vitro than in vivo. This is mainly due to the extremely rapid decay and consequent inactivation of tissue-type plasminogen activator (t-PA), which is the major determinant of thrombolysis, outside the circulation. The degradation of the t-PA can be prevented if a thrombus is formed quickly since the t-PA will rapidly bind to the thrombus and will then be protected from degradation. However, with the known methods, there is a delay of several minutes between withdrawal of blood from a patient and the start of the assay and thrombus formation by which time the concentration of plasma t-PA has already fallen below the level needed for detectable lysis.

SUMMARY OF THE INVENTION

It is an object of the present invention to provide a relevant, accurate and simple method for measuring lysis of a platelet rich thrombus formed under controlled physiologically relevant conditions.

In accordance with one aspect of the invention, a method of forming an occlusive thrombus comprises causing blood to flow under pressure from a non-anticoagulated supply thereof through a capillary tube and into a reservoir such that a thrombus forms in the capillary tube solely by shear-stress, detecting thrombus formation, reducing the pressure and maintaining the reduced pressure for a predetermined period of time.

Apparatus, in accordance with this aspect, comprises a supply of non-anticoagulated blood, means for causing the blood to flow through a capillary tube to a reservoir under pressure, means for detecting the formation of a thrombus in the tube and reducing the pressure when thrombus formation is detected.

The advantage of this is that thrombus formation is carried out in a physiologically relevant manner since it is produced from non-anticoagulated blood by shear-stress alone. Furthermore, the reduction of pressure on completion of formation allows the thrombus to stabilise and more exactly duplicate a natural in vivo thrombus whereby tests carried out thereon will produce more meaningful results.

In accordance with another aspect of the invention, a method of monitoring thrombolysis of an occlusive thrombus comprises forming a thrombus in a capillary tube by flowing non-anticoagulated blood from a sample along the capillary tube, connecting the tube to a supply of anticoagulated blood from the same sample, applying pressure on the thrombus across the anti-coagulated blood and detecting lysis of the thrombus.

Apparatus, in accordance with this aspect of the invention, comprises a supply of non-anticoagulated blood, means for causing the blood to flow through a capillary tube to a reservoir to cause thrombus formation in the tube, the blood being mixed with anticoagulant in the reservoir, means for reversing the direction of blood flow and means for detecting lysis of the thrombus.

An important feature of this aspect is that the blood is mixed with anticoagulant immediately after passing the site of thrombus formation. Accordingly, the anticoagulant will not interfere with either the thrombotic or the thrombolytic process. Furthermore, whilst the thrombus is formed from non-anticoagulated blood, the blood immediately distal to it is protected from coagulation so that it remains in a fluid state during the test. This ensures that an even and well defined pressure can be transmitted through the distal blood onto the thrombus.

In a particularly preferred embodiment, the capillary tube is formed from a thrombogenic material, specifically polyetheretherketone (PEEK) and is relatively long, e.g. 15 mm. This will produce a long thrombus well-adhered to the capillary lumen which, on subjection to pressure, will condense and thus will resist even high back-pressures, for example, pressures of greater than 300 mmHg, without cracking or dislodgement. Thus dislodgement of such a thrombus will only be caused by the specific lytic process. The material and length of the capillary tube will also result in a faster rate of thrombus formation than is achieved with the capillaries of the known methods.

The relatively simple design of the equipment which is a result, in particular, of the use of flow reversal, means that the thrombolysis assay can be easily automated and is simple to carry out. Thus it is suitable for use in the assessment of a large number of subjects.

Suitably, the apparatus comprises a body defining the reservoir and two inlets and an outlet therefor. The capillary tube is attached to the first inlet such that a portion thereof protrudes into the reservoir. The second inlet is connected to a device for supplying metered quantities of anti-coagulant to the reservoir.

The outlet of the reservoir is preferably connected to a second reservoir via a line and a photo-sensor or other detecting device is provided for monitoring the dilution of blood in the line. With this arrangement, the detector can detect both thrombus formation and thrombus lysis. The fact that only a single detector is required is advantageous from the point of view of both simplicity and expense and makes the apparatus readily susceptible to automation.

The means for causing blood to flow may comprise a pump capable of applying pressure across the reservoir and capillary tube and, if provided, the second reservoir and connecting line. Suitably, the pump is capable of applying positive, negative and atmospheric pressure.

Figure 1:
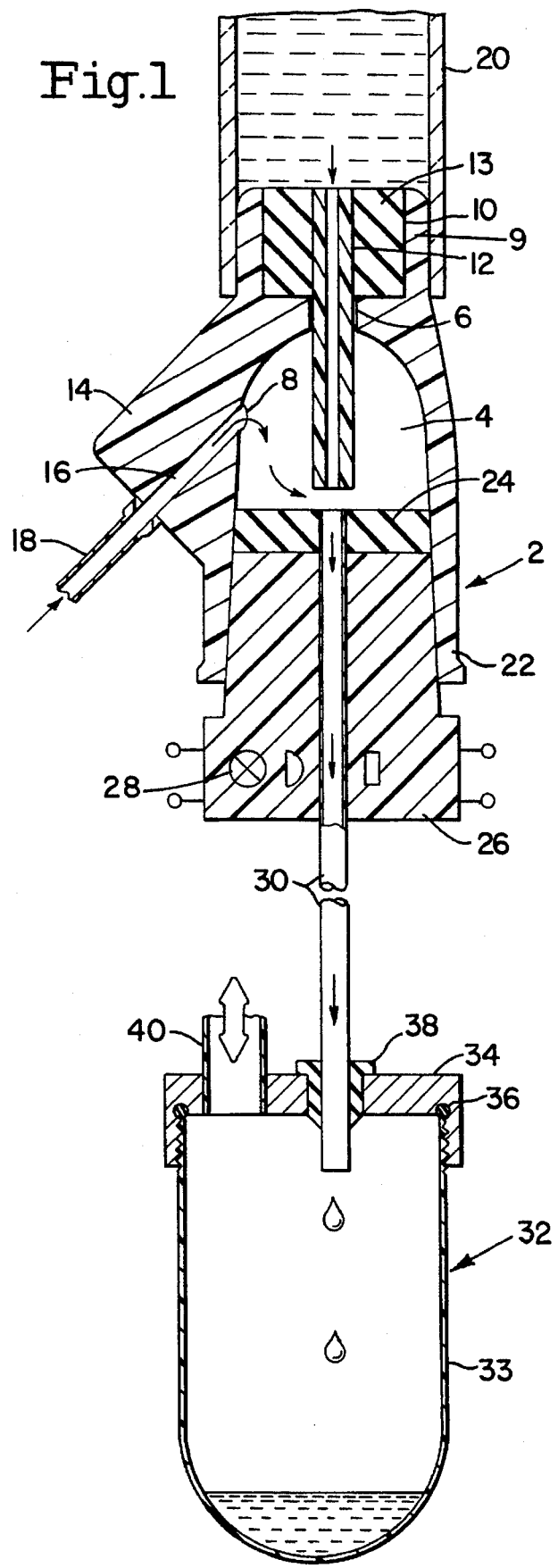
FIG. 1 is a sectional view of the apparatus in accordance with the present invention.

The invention will now be further described by way of example with reference to the accompanying Figure which is a sectional view of apparatus in accordance with the invention.

The body element 2 shown in the Figure has a central chamber 4 with two inlets 6 and 8. The body element 2 extends beyond the first inlet 6, the extension 9 being in the shape of a male Luer fitting with an enlarged central channel 10. A capillary tube 12 is supported within the channel 10 by a piece of silicon rubber tubing 13. The upper end of the capillary tube 12 is aligned with that of the extension 9, whilst the lower end protrudes into the chamber 4 and is aligned with or protrudes below the second inlet 8.

The body element 2 further defines a wing 14 with a channel 16 therethrough which connects the second inlet 8 to a plastic tube 18 which in turn is attached to a micro metering pump (not shown). The micro metering pump is arranged to supply anticoagulant to chamber 4 at a constant rate, e.g. 100 μ/min.

The capillary tube 12 is very preferably formed from polyetheretherketone, PEEK, produced by ICI Company. Suitable dimensions for this are an outer diameter of 1.6 mm, an inner diameter of between 0.125 mm and 0.175 mm and a length of 10–20 mm, preferably 15 mm. PEEK tubing can be cut easily with a blade to any desired length without distorting the capillary inside. PEEK is chemically inert and provides an adhesive surface for activated platelets.

At its upper end, the body element 2 is attached by the male Luer fitting formed by extension 9 to a length of polyethylene tube 20 which serves as a blood container. The upper end of the tube 20 may be provided with a female Luer fitting for connection to a syringe.

The lower end of the body element 2 is in the form of a female Luer fitting 22. The mixing chamber 4 is closed off by a silicon rubber tube 24 carried on a plug element 26, the upper part of which is shaped as a male Luer fitting and is received in female Luer fitting 22. A photo-sensor unit 28 which comprises an infra-red source and integrated photodetector is housed in the lower part of plug element 26. A plastic connecting line 30 is threaded through aligned apertures in the tube 24 and element 26 and extends into a reservoir 32. The line 30 passes through a channel provided in the centre of the sensor unit 28. The reservoir 32 comprises a plastic container 33 threadedly attached to a metal cap 34, the two being sealed by a rubber O-ring 36. A finger-tight grip fitting 38 extends through the cap 34 and serves to provide an airtight connection between the line 30 and the container 33.

A connecting line 40 also extends through the cap 34 and is attached to a pump (not shown) by operation of the valves of which, the reservoir 32, line 30, chamber 4 and capillary tube 12 can be placed under negative pressure, atmospheric pressure and positive pressure.

The thrombolytic activity of a blood sample is measured by carrying out three steps, firstly, formation of a thrombus in the lumen of the capillary tube 12, secondly, stabilisation of the thrombus and, thirdly, dislodgement of that thrombus by pressure.

The blood sample to be tested is withdrawn from a vein, preferably by use of the "2-syringe technique" in which the first 1–2 ml of blood, which is contaminated by contact with the needle and plastic tubing, is discarded or used for other routine haematology measurements. The syringe with the blood sample can then be attached to the tube 20.

By gentle movement of the syringe plunger, blood is pushed from the syringe into the tube 20 leaving an air gap of about 10 mm between the blood column and the upper end of the capillary tube 12. During this process, the system is open, i.e. under atmospheric pressure.

The assay starts by simultaneously applying a negative pressure to the system and activating the micro-metering pump.

The vacuum forces blood in the blood container tube 20 to flow through the capillary 12 and into the chamber 4 where it mixed with the anticoagulant flowing through inlet 8. The resultant anticoagulated blood then passes through line 30 into the reservoir 32. The path of the blood in this stage is shown by the arrows.

As soon as the blood gets into capillary tube 12, the syringe should be disengaged from the blood container tube 20.

Immediately on applying the vacuum, or shortly thereafter, for example five seconds thereafter, the photo-sensor unit 28 is activated. This detects the integrated transmittance per second from the line 30. Once the assay starts, line 30 fills up with blood and, therefore, becomes darker.

The process of thrombus formation will commence in the capillary tube 12 almost immediately as blood platelets aggregate and form a thrombus therein. The increasing occlusion of the capillary lumen will cause a corresponding decrease in the blood flow therethrough. As the rate of infusion of the anticoagulant is constant, the anticoagulated blood which drains through line 30 will consequently become thinner or clearer. The amount of dilution of the blood draining through the line 30 will be directly indicative of the extent to which the capillary lumen has become occluded. The photo-sensor unit 28 is set to detect a dilution which occurs when say about 90% of the capillary lumen has occluded.

When this particular dilution is detected, the photo-sensor unit 28 sends a signal to control means (not shown) which operate the pump to release the vacuum and put the system under atmospheric pressure for a period of about 15 minutes from the start of measurement. During the time that the system is under atmospheric pressure, the labile thrombus which comprises a loose aggregate of platelets gains great structural stability by formation and cross-linking of a fibrin network inside the thrombus around the enmeshed platelets.

During the thrombus stabilisation period, blood cells sediment in the diluted blood in the connecting line 30. As a result, the segment viewed by the photo-detector unit 28 becomes even more transparent whilst the lower end of the line which protrudes into the reservoir 32 becomes dark due to the sedimented red blood cells.

At the end of the stabilisation period, the control means cause the pump to apply a positive pressure on the reservoir 32. The applied pressure is preferably about 150 mmHg since this is the pressure which exists in large arteries. The applied pressure condenses the thrombotic mass making it even more resistant to back pressure so no artificial leakage can occur through the capillary 12. Lysis of the thrombus in the capillary lumen will then occur. As a result of the thrombolysis, the diluted and cell free plasma in the chamber 4 gets through the capillary 12 and the plasma in the line 30 is driven upwards by pressure on the system. The lower part of the blood in the line, which as noted above is darker due to sedimentation, will, therefore, enter the optical path and will be detected by the photo-sensor unit 28. The photo-sensor unit 28 will therefore signal that thrombolysis has occurred and that the assay is at an end. At this time, the control unit will cause the system to be placed under atmospheric pressure to prevent spillage of blood from the tube 20.

The apparatus is capable of full automation. The operator simply has to fill up the blood container tube 20, activate the control means and detach the syringe. After that, no further attention is required as the control means will cause the steps to be automatically performed. The test parameters, in particular the time for thrombolysis to occur, may be automatically noted and stored. When the end of the test is detected, the apparatus can be thrown away safely without danger of blood contamination.

Therefore the apparatus allows tests to be carried out with minimum manpower. Furthermore, the apparatus can particularly efficiently be used in multiple form, i.e. with a number of separate channels, each operating independently but with a single overall control means.

The apparatus can be varied in a number of ways. Firstly, the body element could be inverted so that the blood flow for thrombus formation would be upwards through the capillary tube 12. The blood would mix with the anticoagulant in the chamber 4 around the capillary tube 12. From thence it could be syphoned off to a reservoir by application of pressure across the reservoir-chamber connection. The blood would then be returned to the chamber after disconnection of the capillary 12 from the blood supply and reconnection thereof to a dump line provided with, for example, a photo-detector.

The thrombus, the time of lysis of which is measured, is formed from non-anticoagulated blood by only a single, well defined and physiologically relevant stimulus, specifically, by haemodynamic (shear) forces. The thrombus will be sufficiently firm and stable that it will resist the simulated arterial pressure and will not be torn away but rather will lyse naturally. The thrombus formation starts immediately after the blood sample has been taken so the t-PA level will be preserved and will be equal or close to in vivo levels. The effective transmission of an even and well-defined pressure to the thrombus is ensured by adding the anticoagulant to the blood immediately distal of the thrombus so that this will be anticoagulated, diluted and free from blood cells over the entire test period. The results achieved will, therefore, be an accurate reproduction of the in vivo situation.

Furthermore, the test is readily automated and, in particular with a multi-channel instrument, a large number of subjects can be tested in a relatively short time with minimum operating manpower.

I claim:

1. A method of forming an occlusive thrombus comprising the steps of providing a first supply of blood that has not been clotted or combined with an anticoagulant, causing a portion of said supply of blood to flow under pressure completely through a capillary tube and into a first reservoir such that a thrombus forms in the capillary tube solely by shear-stress optically detecting formation of said thrombus, reducing the pressure after said detecting step detects formation of a complete thrombus and thereafter maintaining the reduced pressure for a predetermined period of time.

2. A method as claimed in claim 1, wherein the pressure is reduced to atmospheric pressure when formation of said thrombus is detected.

3. A method as claimed in claim 2, wherein thrombus formation is detected by mixing the portion of said first supply of blood that flows into said first reservoir with anticoagulant to form a supply of anticoagulated blood, causing part of the thus formed anticoagulated blood to flow from said first reservoir to a second reservoir spaced from said capillary tube via a connecting line and detecting dilution of the blood in said connecting line.

4. A method as claimed in claim 1, wherein the predetermined period of time is about 15 minutes.

5. A method as claimed in claim 1, wherein said first supply of blood is part of a blood sample, wherein the method includes the further steps of connecting said capillary tube to said first reservoir, adding an anticoagulant to said first reservoir and mixing said anticoagulant with said portion of said first supply of blood that has flowed through said tube in order to form a supply of anticoagulated blood in said first reservoir and thereafter increasing the pressure in said first reservoir sufficient to cause said supply of anticoagulated blood to apply force against said formed thrombus.

6. A method as claimed in claim 5, wherein the supply of anticoagulated blood comprises the portion of said first supply of blood which flows into said first reservoir during thrombus formation and is supplied and mixed with said anticoagulant in said first reservoir, and wherein the step of increasing the pressure in said first reservoir includes reversing the direction of blood flow once the thrombus has formed and the predetermined period of time has expired.

7. A method as claimed in claim 1, including detecting lysis of the thrombus.

8. A method as claimed in claim 7, wherein lysis is detected by detecting the dilution of blood flowing in said connecting line between said first reservoir and said second reservoir, said connecting line being subjected to the same pressure as the capillary tube.

9. A method of monitoring thrombolysis of an occlusive thrombus comprising flowing blood that has not been clotted or combined with an anticoagulant from a sample through a capillary tube until a thrombus is formed in said tube, connecting the tube to a reservoir, forming a supply of anticoagulated blood in said reservoir by mixing a portion of said blood with an anticoagulant, increasing the pressure in said reservoir sufficiently to cause said anticoagulated blood supply to apply pressure on the formed thrombus and optically detecting lysis of the thrombus.

10. A method as claimed in claim 9, wherein the thrombus formation is carried out in such a way that the thrombus forms solely by shear-forces and wherein the method includes detecting thrombus formation, reducing the pressure only after the thrombus has been completely formed and maintaining the reduced pressure for a predetermined period of time, thereby to stabilize the thrombus.

11. A method as claimed in claim 10, wherein the pressure is reduced to atmospheric pressure when thrombus formation is detected.

12. A method as claimed in claim 9, wherein the tube is connected to the supply of anticoagulated blood by connecting the tube to said reservoir so that said blood that has not been clotted or combined with an anticoagulant flows thereinto from the tube prior to complete thrombus formation and said anticoagulant is supplied to the reservoir for mixing with the blood therein.

13. A method as claimed in claim 12, wherein the step of increasing the pressure in said reservoir includes reversing the direction of blood flow once the thrombus has formed and the predetermined period has elapsed.

14. A method as claimed in claim 12, wherein thrombolysis is detected by detecting the dilution of blood flowing in said line between the reservoir and a second reservoir, the line being subjected to the same pressures as the capillary tube.

15. A method of monitoring thrombolysis of an occlusive thrombus comprising providing a supply of blood that has not been clotted or combined with an anticoagulant, causing a portion of said blood to flow under pressure from the supply, through a capillary tube and into a reservoir such that a thrombus forms in the capillary tube solely by shear-stress, detecting thrombus formation, reducing the pressure when thrombus formation is detected, maintaining the reduced pressure for a predetermined period of time thereby to stabilize the thrombus, adding anticoagulant to the blood in the reservoir, reversing the direction of the blood flow and optically detecting lysis of the thrombus.

16. Apparatus for measuring the thrombolytic activity of a blood sample comprising a supply of blood that has not been clotted or combined with an anticoagulant, means for causing a portion of said supply of blood to flow from the supply, through a capillary tube such that a thrombus forms in the capillary tube solely by sheer-stress and to a first reservoir under pressure, and a photo detector for detecting the formation of a thrombus in the tube and means for reducing the pressure after complete thrombus formation is detected.

17. Apparatus as claimed in claim 16, further comprising a line connecting said first reservoir to a second reservoir, and means for causing blood flow therein between said first and second reservoirs, said photo detector monitoring the dilution of blood in said line.

18. Apparatus as claimed in claim 16, wherein the means for causing blood to flow comprises a valved pump capable of applying positive, negative and atmospheric pressure across the tube.

19. Apparatus as claimed in claim 16, wherein the capillary tube is formed from polyetheretherketone.

20. Apparatus as claimed in claim 16, wherein the length of the capillary tube is about 15 mm.

21. Apparatus for measuring the thrombolytic activity of a blood sample comprising a supply of blood that has not been clotted or combined with an anticoagulant from the sample, means for causing the blood to flow from the supply, through a capillary tube and to a reservoir to cause thrombus formation in the tube, means for mixing the blood in the reservoir with anticoagulant, means for reversing the direction of blood flow after complete thrombus formation and a photo detector for detecting lysis of the thrombus.

22. Apparatus as claimed in claim 21, including a metering device for supplying metered quantities of anticoagulant to the reservoir.

23. Apparatus as claimed in claim 21, wherein the detection means comprise a line connecting the reservoir to a second reservoir, means for causing blood flow therein between the reservoirs and a detector for monitoring the dilution of blood in the line.

24. Apparatus as claimed in claim 21, wherein the means for causing blood to flow comprises a valved pump capable of applying positive, negative and atmospheric pressure across the tube.

25. Apparatus as claimed in claim 21, wherein the capillary tube is formed from polyetheretherketone.

26. Apparatus as claimed in claim 21, wherein the length of the capillary tube is about 15 mm.

27. Apparatus as claimed in claim 16, wherein said reservoir further comprises means for selectively adding anticoagulant to the portion of said supply of blood that flows to said first reservoir.

* * * * *